United States Patent [19]

Kuroki et al.

[11] 4,152,336
[45] May 1, 1979

[54] AMIDOXIME DERIVATIVES

[75] Inventors: Masataka Kuroki, Sagamihara; Sadamitsu Kono, Machida; Kazuyuki Shioka, Yokohama, all of Japan

[73] Assignee: Sogo Pharmaceutical Company Limited, Sagamihara, Japan

[21] Appl. No.: 885,257

[22] Filed: Mar. 10, 1978

[30] Foreign Application Priority Data

Nov. 9, 1977 [JP] Japan .................................. 52-133621

[51] Int. Cl.$^2$ ............................................ C07D 317/10
[52] U.S. Cl. ........................ 260/340.9 R; 260/307 H; 260/340.7; 260/465.6; 260/564 G
[58] Field of Search ..................... 260/564 G, 340.9 R

[56] References Cited

U.S. PATENT DOCUMENTS

| 3,073,839 | 1/1963 | Kano et al. .......................... 260/307 |
| 3,644,523 | 2/1972 | Neighbors et al. .............. 260/564 G |
| 3,984,470 | 10/1976 | Binon et al. ...................... 260/564 G |

Primary Examiner—Ethyl G. Love
Attorney, Agent, or Firm—Browdy and Neimark

[57] ABSTRACT

Novel amidoxime derivatives having the following structural formula (IV) of (IV'):

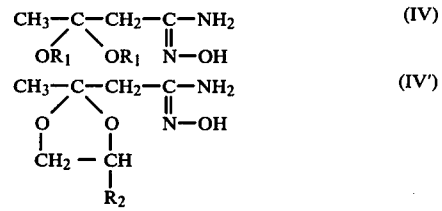

wherein $R_1$ represents methyl or ethyl group and $R_2$ represents hydrogen or methyl group, useful as a raw material for 3-amino-5-methyl isoxazole, are prepared from β-amino crotonitrile. Said isoxazole, useful as an intermediate for various medicines, may be prepared without producing any by-products of isomer.

1 Claim, No Drawings

AMIDOXIME DERIVATIVES

The present invention relates to a novel amidoxime and a method for preparing the same. The amidoxime of the present invention is a useful raw material for 3-amino-5-methyl isoxazole which is an intermediate for various medicines such as sulfonamide. Therefore, the present invention also relates to a novel and useful method for preparing the above mentioned isoxazole.

We tried to prepare 3-amino-5-methyl isoxazole by using acetoacetonitrile as the starting material. In case of that the starting material was reacted with hydroxylamine without any chemical protection of carbonyl group of the starting material, hydroxylamine is preferentially reacted with carbonyl group rather than nitrile group and therefore the objective compound was little prepared. Then, we tried the reaction by using the starting material having carbonyl group previously protected. Even in this case we were not able to obtain the objective substance.

However, we have eagerly researched this reaction and found that the preparative substance of this reaction is an amidoxime derivative which is a novel compound, not having written in any literatures, in which hydroxylamine is attached to nitrile group. Furthermore, we have found that the novel amidoxime derivatives can be easily and selectively converted to 3-amino-5-methyl isoxazole by treating in an acidic condition. It is a surprising fact that the yield of isomer, namely 5-amino-3-methyl isoxazole, is not substantially recognized, as compared with the fact that the known similar reactions always give relatively large amounts of isomers.

Accordingly, an object of the present invention is to provide novel amidoxime derivatives.

An other object of the present invention is to provide a method for preparing the same.

A further object of the present invention is to provide an effective method for preparing 3-amino-5-methyl isoxazole, which is useful as an intermediate for various medicaments and the like.

The method according to the present invention is shown as the following equations.

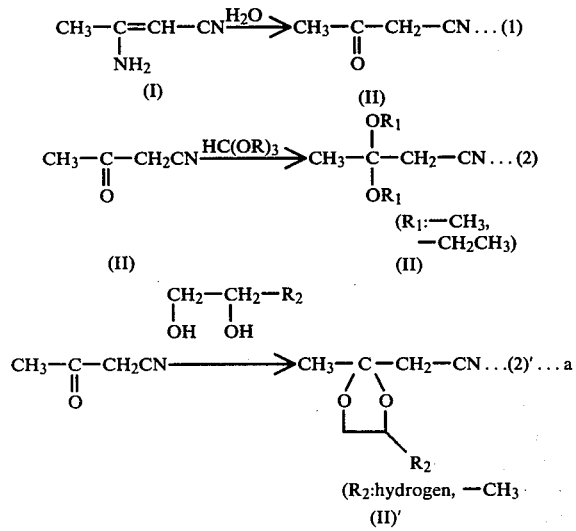

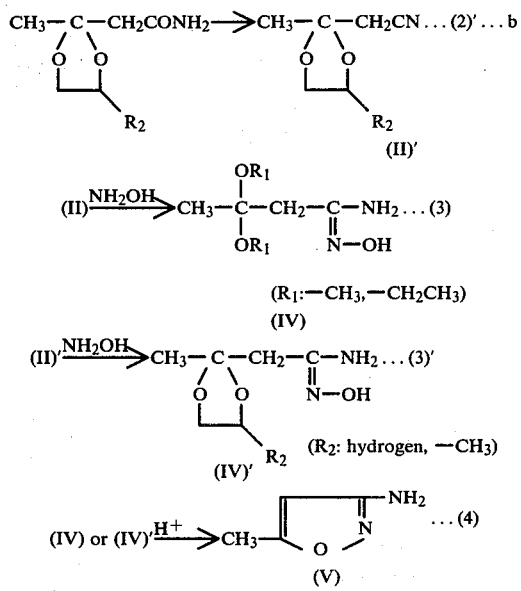

As shown above, according to the present invention, β-aminocrotonitrile (namely diacetonitrile) (I) is hydrolyzed to produce acetoacetonitrile (II), the obtained compound (II) is reacted with trialkyl orthoformate or ethyleneglycol derivatives in the presence of an acid catalyst to produce β-dialkoxy acetoacetonitrile (III) or β-ethylenedioxy acetoacetonitrile derivatives(III'), or ethylenedioxy butyramide is dehydrated using a dehydrating agent to produce β-ethylenedioxy acetoacetonitrile derivatives(III'), the obtained (III) or (III') is reacted with hydroxylamine in the presence of an alkaline substance to produce β-dialkoxy aceto-acetamidoxime (IV) or β-ethylenedioxy acetoacetamidoxime derivatives(IV') and the obtained compound (IV) or (IV') is treated in an acidic condition to be converted to 3-amino-5-methyl isoxazole.

The novel amidoxime derivatives thus obtained are colorless, transparent and viscous liquids or white crystals.

The methods according to the present invention are preferably conducted as follows. The hydrolysis of β-aminocrotonitrile is, first of all, carried out in an aqueous solution in an acidic condition of hydrochloric acid at 50°–100° C. for 1–5 hours. More preferably, the hydrolysis is conducted at 80° C. for a period of 2 hours, and, after completion of the reaction, the product is extracted with ethyl acetate and then vacuum-distilled to obtain acetoacetonitrile. Although it has been previously known that acetoacetonitrile is much polymerizable, we have found that it is stable under a weak acidic condition and can be stored for a long period of time. Then, acetoacetonitrile and trialkyl orthoformate or ethyleneglycol derivatives are reacted in the presence of an acid catalyst to produce ketal compound of acetoacetonitrile. As the trialkyl orthoformate, trimethyl orthoformate and triethyl orthoformate are preferably used, and as the ethyleneglycol derivatives ethyleneglycol and propyleneglycol are preferably used owing to their availability. Among them, ethyleneglycol is the best. As the acid catalyst, mineral acids and sulfonic acids such as hydrochloric acid, hydrogen chloride, sulfuric acid, benzene-sulfonic acid and p-toluene-sulfonic acid are preferably used. As the reaction medium, lower alcohols and aromatic hydrocarbons, such as methanol, ethanol, benzen, toluene and xylene, are preferably used. The reaction temperature and the reaction time are not limited. However when using trialkyl orthoformate, the reaction is preferably conducted at about room temperature for a few hours, and when using ethyleneglycol derivatives, the reaction is preferably conducted at the boiling point of a solvent used as the reaction medium while water is removed azeotropically. Usually, the reaction is finished in a few hours. After completion of the reaction, according to conventional method, the solvent is distilled out and then the objective compound, namely ketal compound of acetoacetonitrile is obtained by vacuum distillation. β-Ethylenedioxy acetoacetonitrile derivatives are also prepared by reacting β-ethylenedioxy butyramide with phosphorus pentaoxide in the presence of triethyl amine. In this reaction, a reaction solvent is not necessarily used but preferably used in order to proceed smoothly the reaction. As the solvent, inert organic solvents, such as benzene, are preferably used. The reaction is preferably conducted at a temperature of from about room temperature to about 100° C., the solvent is distilled out after completion of the reaction and then β-ethylenedioxy acetoacetonitrile is obtained by vacuum distillation.

Ketal of acetoacetonitrile thus obtained is reacted with hydroxylamine in the presence of an alkaline substance to produce a novel compound, ketal of acetoacetamidoxime. As the alkaline substance to be used in this reaction, alkali metal hydroxides and alkali metal alkoxides are preferably used. Among them, sodium hydroxide and sodium methylate are more preferably used owing to their availability. As the reaction solvent to be used in this reaction, various solvents such as lower alcohols, water and mixtures thereof may be used. Among them, methanol, water and mixture thereof are more preferably used. The reaction temperature and the reaction time are not necessarily limited, but −10°–100° C. and a few—ten or more hours are usually preferable. The amount of the alkaline substance is preferably 1–4 moles to 1 mole of ketal of acetoacetonitrile and the amount of hydroxylamine is preferably 1–3 moles thereto. After completion of the reaction, distilling out of the solvent, extraction by ethyl acetate and distilling out of ethyl acetate are conducted and the residue obtained thereafter contains a great part of the objective compound, ketal of acetoacetamidoxime. The compound thus obtained can be distilled or recrystallized but can be directly used in the next reaction without any purification.

Ketal of acetoacetamidoxime thus obtained is subjected to ring-closing reaction using an acid catalyst. As the acid catalyst to be used in this reaction, mineral acids, especially hydrochloric acid, are preferably used. As the reaction solvent to be used in this reaction, lower alcohol, water and mixture thereof are preferably used. The reaction is preferably conducted at about room temperature −100° C. for a few hours. After completion of the reaction, 3-amino-5-methyl isoxazole can be obtained in accordance with conventional methods. In this case, one of the greatest features of the present invention is the fact that useless isomer, 5-amino-3-methyl isoxazole, is not be substantially produced.

Conventional methods for preparing 3-amino-5-methyl isoxazole are, for example, (a) a method in which propiolonitrile derivatives are reacted with hydroxylamine in the presence of alkali metal hydroxide (Japanese Patent Publication No. 42-23191), (b) a method in which halogen-carbonitrile is reacted with hydroxylamine or hydroxylamine having protected amino group in an alkaline medium (Japanese Patent Publication No. 41-21147), and (c) a method in which alkyl ester of acylpyruvic acid is converted to 5-alkyl-3-carboalkoxy isoxazole, its amide and then its amine (Japanese Patent Publication No. 37-17231, 37-4886, 37-4887). In case of (a), the starting material is not available and the yield of the objective compound is low, and in case of (b) and (c), a large amount of isomers such as 5-amino-3-methyl isoxazole is necessarily produced. They have such disadvantages as using expensive derivative of hydroxylamine and controlling strictly the reaction condition in order to prevent the yield of the isomer.

However, the present invention shows such great advantages that by-production of isomer, 5-amino-3-methyl isoxazole, is not accompanied at all and 3-amino-5-methyl isoxazole is selectively obtained with high yield.

Moreover, β-aminocrotonitrile, the starting material, is a compound easily manufactured as compared with acetonitrile, one of the typical petrochemical goods, and therefore, the present invention shows such advantage that an inexpensive and easily available compound is used as the starting material.

Moreover, the present invention shows such advantage that the novel compounds, amidoxime derivatives, can be converted easily to 3-amino-5-methyl isoxazole which is an essential compound for preparing useful sulfametoxazole, one of durable sulfonamides. Hereinafter, the present invention is explained by Examples.

EXAMPLE 1

41 grams of β-aminocrotonitrile were dissolved in a mixture of 50cc of water and 50cc of concentrated hydrochloric acid and reacted at 80° C. for 2 hours.

After cooling, the precipitate was filtered and extracted with ethyl acetate followed by distilling out of the solvent and vacuum distillation, and 34.5 grams of acetoacetonitrile of colorless transparent liquid (bp 73°–75° C./6mm Hg) were obtained. (Yield 84.15%)

EXAMPLE 2

34.5 grams of acetoacetonitrile were dissolved in 100ml of methanol, 66 grams of methyl orthoformate and 10 drops of concentrated sulfuric acid were added thereto and stirred for a night. After completion of the reaction, 0.5 grams of potassium carbonate was added thereto and stirred for 30 minutes to neutralize. Methanol was distilled out by means of an evaporator and 48.5 grams of β-dimethoxy acetoacetonitrile of colorless transparent liquid (bp 58°–60° C./7mm Hg) were obtained. (Yield 90.3%)

EXAMPLE 3

16 grams of acetoacetonitrile were dissolved in 50cc of ethanol, and 42 grams of ethyl orthoformate and 5 drops of sulfuric acid were added thereto. After completion of the reaction, 0.5 grams of potassium carbonate was added thereto and stirred for 30 minutes to neutralize.

Ethanol was distilled out by means of evaporator and 22 grams of β-diethoxy acetoacetonitrile of colorless transparent liquid were obtained by vacuum distillation (bp 48°–50° C./4.5mm Hg). (Yield 72.6%)

EXAMPLE 4

33.2 grams of acetoacetonitrile were dissolved in 200ml of benzene, 28 grams of ethylene glycol and 0.2 gram of para-toluene sulfonic acid were added thereto and water produced through the reaction was distilled out with benzene. The terminal point of the reaction was checked by the amount of water distilled out. The remaining benzene was distilled out by means of an evaporator and 47.7 grams of β-ethylenedioxy acetoacetonitrile of colorless transparent liquid were obtained by vacuum distillation. (bp 63°–66° C./7mm Hg) (Yield 93.9%)

EXAMPLE 5

Using 63 grams of acetoacetonitrile, 60 grams of propylene glycol, 200ml of toluene and 0.2 gram of paratoluene sulfonic acid, the same procedure as shown in Example 4 was conducted and 104 grams of β-propylenedioxy acetoacetonitrile of colorless transparent liquid were obtained. (bp 70°–75° C./6mm Hg) (Yield 96.3%)

EXAMPLE 6

103 grams of β-ethylenedioxy butyramide were dissolved in a mixture of 250ml of benzene and 145 grams of triethyl amine, and 13.5 grams of phosphorus pentaoxide were gradually added thereto. The temperature was gradually elevated to reflux for 1 hour, and benzene and triethyl amine were recovered. The residue was vacuum-distilled and 79.4 grams of β-ethylenedioxy acetoacetonitrile were obtained. (Yield 87.4%)

EXAMPLE 7

Into 50ml of water 10 grams of sodium hydroxide were dissolved, then after addition of 50ml of methanol, 13.5 grams of hydroxylamine hydrochloride were dissolved under an ice-cooled condition. Finally 12.9 grams of β-dimethoxy acetoacetonitrile were dropped thereto and stirred for one night at a room temperature. After reflux for 2 hours as a post-reaction, the product was extracted with ethyl acetate and 11 grams of β-dimethoxy acetoacetamidoxime of colorless, transparent and viscous liquid were obtained therefrom. (bp 104°–114° C./7mm Hg) (Yield 67.9%)

Elemental Analysis

| | $C_6H_{14}O_3N_2$ | | |
|---|---|---|---|
| | C | H | N |
| calcd. | 44.4 % | 8.6 % | 173. % |
| found | 45.16 % | 8.49 % | 17.03 % |

EXAMPLE 8

Using 10 grams of sodium hydroxide, 100 ml of water, 100ml of methanol, 27 grams of hydroxylamine hydrochloride and 31.5 grams of β-diethoxy acetoacetonitrile, the procedure shown in Example 7 was repeated, then 20.5 grams of β-diethoxy acetoacetamidoxime of white needle crystal were obtained. (mp 111° C.) (Yield 54%)

Elemental Analysis

| | $C_8H_{18}O_3N_2$ | | |
|---|---|---|---|
| | C | H | N |
| calcd. | 50.5 % | 9.5 % | 14.7 % |
| found | 50.43 % | 9.69 % | 14.73 % |

EXAMPLE 9

Using 50 grams of sodium hydroxide, 250 ml of water, 250ml of methanol, 67.5 grams of hydroxylamine hydrochloride and 55 grams of β-ethylenedioxy acetoacetonitrile, the procedure shown in Example 7 was conducted and 51.8 grams of β-ethylenedioxy acetoacetamidoxime were obtained after recrystallization. (mp 71° C.) (Yield 74.5%)

Elemental Analysis

| | $C_6H_{12}O_3N_2$ | | |
|---|---|---|---|
| | C | H | N |
| calcd. | 45.0 % | 7.5 % | 17.5 % |
| found | 45.02 % | 7.54 % | 17.35 % |

EXAMPLE 10

Using 60 grams of sodium hydroxide, 300 ml of water, 300ml of methanol, 70 grams of hydroxylamine hydrochloride and 71 grams of β-propylenedioxy acetoacetonitrile, the procedure shown in Example 7 was conducted and 65.6 grams of β-propylenedioxy acetoacetamidoxime of colorless, transparent, viscous liquid were obtained by vacuum distillation. (bp 131°–136° C./7mm Hg) (Yield 75%)

Elemental Analysis

| | $C_7H_{14}O_3N_2$ | | |
|---|---|---|---|
| | C | H | N |
| calcd. | 48.3 % | 8.0 % | 16.1 % |
| found | 48.32 % | 8.02 % | 16.22 % |

EXAMPLE 11

Using 10 grams of sodium hydroxide, 100 ml of water, 13.5 grams of hydroxylamine hydrochloride and 12.9 grams of β-dimethoxy acetoacetonitrile but no methanol, the procedure shown in Example 7 was conducted for 89 hours. The solvent was distilled out and the residue was vacuum distilled and 5.2 grams of β-dimethoxy acetoacetamidoxime of colorless, transparent and viscous liquid were obtained. (bp 111° C./7mm Hg) (Yield 60.5%)

EXAMPLE 12

Into 100ml of ethanol 11.2 grams of sodium methylate were dissolved and methanol solution containing 10.4 grams of hydroxylamine hydrochloride were dropped thereto under an ice-cooled condition and 13 grams of β-dimethoxy aceto-acetonitrile were dropped thereto, followed by the procedure shown in Example 7, and 11.9 grams of β-dimethoxy acetoacetamidoxime of colorless, transparent and viscous liquid were obtained. (Yield 56.0%)

EXAMPLE 13

Into 100ml of ethanol, metal sodium was dissolved, methanol solution containing 15 grams of hydroxylamine hydrochloride was added thereto under an ice-cooled condition and 22 grams of β-diethoxy acetoacetonitrile were dropped thereto, followed by the same procedure as shown in Example 7, 16 grams of β-diethoxy acetoacetamidoxime of white solid were obtained. (mp 111° C.) (Yield 60%)

EXAMPLE 14

Into 100ml of butanol 4.6 grams of metal sodium were dissolved, methanol solution containing 10.4 grams of hydroxylamine hydrochloride were dropped thereto under an ice-cooled condition and 13 grams of β-dimethoxy acetoacetonitrile were added thereto, followed by the same procedure as shown in Example 7, 10.1 grams of β-dimethoxy acetoacetamidoxime of colorless, transparent and viscous liquid were obtained by vacuum distillation. (Yield 60%)

EXAMPLE 15

Into 20ml of ethanol 3.2 grams of β-dimethoxy acetoacetamidoxime were dissolved and a few drops of concentrated hydrochloric acid was added thereto and stirred for 2 hours and left as it was for one night. The product was extracted with ethyl acetate and 1.9 grams of 3-amino-5-methyl isoxazole of pale yellow solid was obtained therefrom. (Yield 96.9%)

EXAMPLE 16

Into 100ml of ethanol 9 grams of β-diethoxy acetoacetamidoxime were dissolved and the same procedure shown in Example 15 was conducted. 4 grams of 3-amino-5-methyl isoxazole were obtained. (Yield 85.2%)

EXAMPLE 17

Using 16 grams of β-ethylenedioxy acetoacetamidoxime and 100ml of ethanol, the same procedure as shown in Example 15 was conducted, and 5.9 grams of 3-amino-5-methyl isoxazole were obtained. (Yield 60%)

EXAMPLE 18

Using 17.5 grams of β-propylenedioxy acetoacetamidoxime and 100ml of ethanol, the same procedure as shown in Example 15 was conducted, and 12.2 grams of 3-amino-5-methyl isoxazole were obtained. (Yield 80%)

APPLICATION EXAMPLE

Onto 7 grams of pyridine 4 grams of 3-amino-5-methyl isoxazole above obtained were added and heated to 40° C. p-Acetylaminobenzene sulfonyl chloride was added thereto in 6 times in a total amount of 10.5 grams while maintaining the temperature between 40° C. and 50° C. After adding the total amount of 10.5 grams of p-acetylamino benzen sulfonyl chloride, the liquid temperature is elevated to 65°-70° C., and the reaction was carried out for 3 hours.

Thereafter, 30ml of hot water of more than 60° C. were added thereto and 60°-65° C. was kept for 30 minutes and then cooled to below 40° C. Then the pH thereof was adjusted to 3.6 by adding 30% $H_2SO_4$ and the product was filtered, washed and dried to obtain 11 grams of 3-p-acetyl-amino-benzene-sulfonamide-5-methyl isoxazole.

11 grams of the acetyl compound thus obtained were added into NaOH aqueous solution (NaOH 4 grams, water 32 grams) and heated for 1 hour. After cooling, the pH of the reaction solution was adjusted to 5 to deposit white crystal. 8.0 grams of the pure product (mp 167.6°-168.2° C.) were obtained by recrystallization from alcohol. The IR and TLC values of the product was completely identical with the standard sample. (Yield 75.8%)

What is claimed is:

1. Amidoxim derivatives having the formula

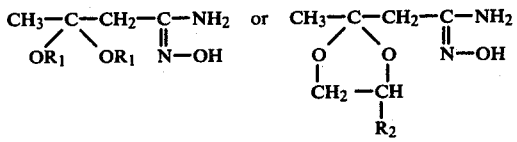

wherein $R_1$ is methyl group or ethyl group and $R_2$ is hydrogen or methyl group.

* * * * *